US011141736B2

(12) United States Patent
Gaebele

(10) Patent No.: US 11,141,736 B2
(45) Date of Patent: Oct. 12, 2021

(54) MICRONIZER

(71) Applicant: Klafs GmbH & Co. KG, Schwaebisch Hall (DE)

(72) Inventor: Markus Gaebele, Schwaebisch Hall (DE)

(73) Assignee: Klafs GmbH & Co. KG, Schwaebisch Hall (DE)

( * ) Notice: Subject to any disclaimer, the term of this patent is extended or adjusted under 35 U.S.C. 154(b) by 280 days.

(21) Appl. No.: 16/091,625

(22) PCT Filed: Oct. 27, 2016

(86) PCT No.: PCT/EP2016/075904
§ 371 (c)(1),
(2) Date: Oct. 5, 2018

(87) PCT Pub. No.: WO2017/174164
PCT Pub. Date: Oct. 12, 2017

(65) Prior Publication Data
US 2019/0118186 A1 Apr. 25, 2019

(30) Foreign Application Priority Data
Apr. 7, 2016 (DE) ..................... 10 2016 106 358.4

(51) Int. Cl.
*B02C 17/00* (2006.01)
*B02C 17/10* (2006.01)
(Continued)

(52) U.S. Cl.
CPC ............. *B02C 17/005* (2013.01); *A47J 42/06* (2013.01); *A61J 3/02* (2013.01); *A61M 15/0006* (2014.02);
(Continued)

(58) Field of Classification Search
CPC ... B02C 17/005; B02C 17/10; B02C 17/1805; B02C 17/1865; B02C 17/24;
(Continued)

(56) References Cited

U.S. PATENT DOCUMENTS 1,894,106 A * 1/1933 Lehrack .................. B02C 15/10 241/172
2,350,534 A * 6/1944 Rosinger ............. B01F 13/0818 366/274
(Continued)

FOREIGN PATENT DOCUMENTS

DE 81500 C 11/1894
DE 4003989 A1 * 8/1991 .......... A61M 16/108
(Continued)

OTHER PUBLICATIONS

Umit Baba—Youtube Channel (Home made Regulable Rheostat). "https://www.youtube.com/watch?v=pdvgtJv7Uio" (Year: 2015).*
(Continued)

*Primary Examiner* — Shelley M Self
*Assistant Examiner* — Smith Oberto Bapthelus
(74) *Attorney, Agent, or Firm* — Jason H. Vick; Sheridan Ross, PC

(57) ABSTRACT

Apparatus for micronizing an inorganic salt, having a receiving vessel for receiving the salt to be micronized in an interior of the receiving vessel; a grinding unit for comminuting the salt located in the receiving vessel and for forming micronized salt particles; an ascending pipe, which is connected fluidically to the receiving vessel and transports the micronized salt particles, wherein one end of the ascending pipe has an outlet orifice through which the micronized salt particles can flow out of the apparatus; a fan; and a housing with an air outlet and an air duct connecting the fan to the air outlet, wherein the air duct is separated by at least
(Continued)

one wall from the interior of the receiving vessel, such that the air stream generated by the fan does not flow through the interior of the receiving vessel.

13 Claims, 6 Drawing Sheets

(51) Int. Cl.

| | |
|---|---|
| ***A47J 42/06*** | (2006.01) |
| ***A61J 3/02*** | (2006.01) |
| ***B02C 15/10*** | (2006.01) |
| ***A61M 15/02*** | (2006.01) |
| ***A61M 15/00*** | (2006.01) |
| ***B02C 23/20*** | (2006.01) |
| ***B02C 17/18*** | (2006.01) |
| ***B02C 17/24*** | (2006.01) |

(52) U.S. Cl.
CPC ........ *A61M 15/0065* (2013.01); *A61M 15/02* (2013.01); *B02C 15/10* (2013.01); *B02C 17/10* (2013.01); *B02C 17/1805* (2013.01); *B02C 17/1865* (2013.01); *B02C 17/24* (2013.01); *B02C 23/20* (2013.01); *A61M 2202/066* (2013.01); *A61M 2206/18* (2013.01)

(58) Field of Classification Search
CPC .......... A61M 15/0006; A61M 15/0065; A61M 15/02; A61M 2202/066
USPC ........................................... 241/36, 170–173
See application file for complete search history.

(56) References Cited

U.S. PATENT DOCUMENTS

| | | | | |
|---|---|---|---|---|
| 3,570,819 | A * | 3/1971 | Rosinger | B01F 15/00915 366/274 |
| 5,014,611 | A * | 5/1991 | Illy | A47J 31/402 99/280 |
| 5,080,093 | A * | 1/1992 | Raabe | A61M 15/00 128/200.21 |
| 5,322,057 | A * | 6/1994 | Raabe | A61M 15/00 128/200.16 |
| 5,747,002 | A | 5/1998 | Clark et al. | |
| 2013/0125888 | A1 | 5/2013 | Monterenzi | |

FOREIGN PATENT DOCUMENTS

| | | | | |
|---|---|---|---|---|
| DE | 102004059530 A1 | 7/2005 | | |
| DE | 102012111431 A1 | 5/2014 | | |
| EP | 2457559 A1 | 5/2012 | | |
| WO | WO 2007/054604 | 5/2007 | | |
| WO | WO 2008/084269 | 7/2008 | | |
| WO | WO-2008084269 A2 * | 7/2008 | .......... | A61M 11/042 |
| WO | WO 2011/100981 | 8/2011 | | |
| WO | WO 2014/080035 | 5/2014 | | |
| WO | WO 2015/006838 | 1/2015 | | |

OTHER PUBLICATIONS

International Search Report for International Application No. PCT/EP2016/075904, dated Mar. 10, 2017.
Written Opinion for International Application No. PCT/EP2016/075904, dated Mar. 10, 2017.
International Preliminary Report on Patentability for International Application No. PCT/EP2016/075904, dated Oct. 18, 2018.

* cited by examiner

MICRONIZER

CROSS REFERENCE TO RELATED APPLICATIONS

This application is a national stage application under 35 U.S.C. 371 of PCT Application No. PCT/EP2016/075904 having an international filing date of 27 Oct. 2016 which designated the United States, which PCT application claimed the benefit of German Application No. 10 2016 106 358.4 filed 7 Apr. 2016, each of which are incorporated herein by reference in their entirety.

The present invention relates to an apparatus for micronizing an inorganic salt. Such an apparatus is often also known as a micronizer and serves to produce salt particles in the micrometer and submicrometer range to produce airborne salt particulates or a salt aerosol.

Such micronizers are conventionally used in salt caves, where the salt aerosol can be inhaled. This may be done for medical or cosmetic purposes, but also purely for wellness purposes. Micronizers are also increasingly used in saunas or other wellness facilities for the above-stated purposes.

To be effective as an aerosol in such facilities, the salt particles present in the aerosol should have an average particle diameter of around 2 μm, preferably of less than 2 μm, such that they can penetrate as deep as possible into the pulmonary airways.

Various technologies already exist for producing micronized salt particles with average particle diameters within the above-stated value range.

For example, DE 10 2004 059 530 A1 describes an apparatus for producing a salt aerosol, in which the grinding process is performed by a rapidly rotating grinding tool. The apparatus described in this document has the disadvantage, however, that grinding is here performed using a mechanical grinding apparatus, which is disadvantageous on the one hand in terms of wear to the grinding apparatus and also the introduction of impurities, whether from the grinding tool or from lubricants from the drive. It has furthermore also been demonstrated that such apparatuses display only limited suitability for continuous operation due to the relatively frequent maintenance intervals, attributable inter alia also to the use of corrosive common salt. Finally, these apparatuses also have the disadvantage of being relatively noisy, such that such an apparatus tends to be perceived as troublesome when used in a wellness facility.

U.S. Pat. No. 5,747,002 describes an apparatus for producing a salt aerosol using a jet mill principle. In this apparatus, grinding is performed according to the countercurrent principle, followed by cyclone-based classification. Although jet mills do not in general have some of the above-described disadvantages, the apparatus disclosed in U.S. Pat. No. 5,747,002 A does have the disadvantage on the one hand that the design thereof is relatively complex and on the other hand that gases are used therein under high pressure, which leads to high energy consumption and to a safety risk. In addition, this apparatus also enables the production only of particles with a diameter of around 7 μm.

EP 2 457 559 A1 describes a further apparatus for producing a salt aerosol. The salt to be micronized is in this case present in a retaining stage and is subjected to a grinding process. A separating stage is arranged with the retaining stage, the grinding stage and a gas supply upstream of the retaining stage in such a way that the gas flows through the grinding apparatus along the longitudinal axis thereof. The selected design of this apparatus makes it difficult, however, to ensure a more or less uniform particle size of the salt particles contained in the salt aerosol produced. To prevent undesirably large salt particles from flowing out of the apparatus, screens or baffle plates have here specially to be used.

It is thus an object of the present invention to provide an apparatus for micronizing an inorganic salt and for producing a salt aerosol which overcomes the above-stated disadvantages. It is here in particular an object of the present invention to improve such an apparatus in terms of the reliability with which salt particles present in the salt aerosol can be produced with maximally uniform particle sizes and in terms of cleanability, hygiene, noise emission, maintenance intensity and manufacturing costs.

This object is achieved by an apparatus herein, wherein this apparatus comprises the following:

a receiving vessel for receiving the salt to be micronized in an interior of the receiving vessel;

a grinding unit for comminuting the salt to be micronized located in the receiving vessel and for forming micronized salt particles;

an ascending pipe, which is connected fluidically to the receiving vessel and serves to transport the micronized salt particles, wherein one end of the ascending pipe has an outlet orifice through which the micronized salt particles can flow out of the apparatus;

a fan for generating an air stream; and a housing with an air outlet and an air duct connecting the fan to the air outlet, wherein the air duct is separated by at least one wall from the interior of the receiving vessel, such that the air stream generated by the fan does not flow through the interior of the receiving vessel, and wherein the air outlet at least partly surrounds the ascending pipe in a region of the outlet orifice.

The apparatus according to the invention is distinguished in particular by the novel manner of air conduction within the housing compared with the prior art. That is to say, the receiving vessel, into which the salt to be micronized is conventionally introduced before the apparatus is started up, is not flowed through directly by the air stream generated by the fan, as is generally the case with such apparatuses. Instead, an air duct is provided in the housing which is separated from the interior of the receiving vessel by at least one wall. This air duct leads within the housing of the apparatus from the fan to an air outlet. The air outlet at least partly surrounds an ascending pipe, which is connected to the receiving vessel and in which the micronized salt particles comminuted by the grinding unit ascend. More precisely, the air outlet surrounds the ascending pipe in the region of the outlet orifice through which the micronized salt particles flow out of the apparatus. The air stream generated by the fan and the micronized salt particles are thus brought together in the region of the outlet orifice arranged at the upper end of the ascending pipe.

The above-mentioned arrangement of the air duct and the avoidance of direct flow through the receiving vessel result in the following advantages: on the one hand a suction effect is produced in the interior of the ascending pipe by the flow around the outlet orifice, which suction effect preferably only becomes effective in the upper part of the ascending pipe, i.e. in the vicinity of the outlet orifice. This type of suction flow, which is induced in the upper part of the ascending pipe, acts only on the salt particles which have already been sufficiently comminuted in the grinding unit and have ascended, due to the acceleration thereof contrary to gravity experienced within the grinding unit, to a given height in the interior of the receiving vessel and of the adjoining ascending pipe. This in turn ensures that undesirably large salt particles are not caught up at all by the above-mentioned suction flow and thus also do not flow out of the apparatus, since these relatively large salt particles do not ascend far enough in the receiving vessel and the adjoining ascending pipe due to their relatively heavier weight. To conclude, compliance with a maximum particle size for the outflowing salt particles may thus be guaranteed.

The type of air conduction according to the invention within the apparatus has the additional advantage that the salt located in the apparatus is shielded in a way from the fan, since the air stream is conveyed separately from the salt particles within the apparatus in the manner of a bypass. This is in turn associated with hygiene-related advantages and also has a positive effect in terms of maintenance intensity due to a lower susceptibility to corrosion.

A further advantage of the apparatus according to the invention lies in its comparatively inexpensive manufacture and the comparatively simple cleanability of the apparatus, since for example, compared with the apparatus known from EP 2 457 559 A1, no screens or baffle plates have to be specially provided in the ascending pipe.

According to a refinement of the present invention, the air outlet of the air duct is arranged concentrically with the outlet orifice of the ascending pipe, wherein the air outlet completely surrounds the outlet orifice.

This refinement has the advantage that the above-described suction flow, which is induced in the upper region of the ascending pipe, takes effect over the entire diameter of the ascending pipe. This leads to relatively good distribution of the micronized salt particles flowing out of the apparatus. In addition, the intensity with which the micronized salt particles flow out of the apparatus may also be relatively well regulated by the above-mentioned principle.

According to a further refinement of the present invention, the grinding unit comprises (i) a motor, (ii) a magnet driven rotationally by the motor and (iii) a ball of magnetizable material, wherein the ball is arranged within the receiving vessel and the motor and the magnet driven thereby are arranged outside the receiving vessel, and wherein the ball is moved relative to the receiving vessel by the rotation of the magnet. In this respect, it is particularly preferable for the grinding unit to comprise precisely one ball of magnetizable material.

This refinement has the advantage that contactless drive of the grinding unit is ensured thereby, "contactless" here being understood to mean that there is no direct, mechanical contact between the ball located in the receiving vessel and the drive with motor and magnet connected thereto conventionally arranged beneath the receiving vessel. This is in turn advantageous for reasons of hygiene, since the salt located in the receiving vessel cannot be contaminated by lubricating greases or oils to be found in the region of the drive. Moreover, the risk of corrosion of the drive parts of the grinding unit may also be enormously reduced. It has additionally been found to be advantageous that this type of grinding unit with magnetically driven ball is relatively quiet compared with other grinding apparatuses known in the art.

When a grinding unit with magnetically driven ball is used as stated, a plurality of effects work towards comminution of the salt to be micronized or formation of the micronized salt particles: on the one hand, the salt grains are set in motion by the ball rotating in the receiving vessel, whereby they bump into one another and also into the internal wall of the receiving vessel. The salt grains thereby crush and pulverize one another. To a lesser extent, the salt grains are also ground between the ball and the internal wall of the receiving vessel.

According to one preferred refinement, the receiving vessel has a closed, round bottom face.

This guarantees that the ball may move over a circular path at relatively high speeds. Due to the centrifugal force acting on the ball during rotational drive of the ball, the latter conventionally moves along the outer edge of the bottom face with support from the internal walls of the receiving vessel.

According to a further refinement, provision is made for the diameter of the bottom face to correspond to at least 5 times, preferably at least 10 times the diameter of the ball.

The ball is thus preferably selected to be very small in comparison with the diameter of the receiving vessel. The receiving vessel itself is preferably cylindrical in shape. A conical shape would however likewise be feasible for the receiving vessel.

According to a further refinement, the motor has a motor shaft on which the magnet is arranged eccentrically, wherein the grinding unit additionally has a counterweight which corresponds approximately to the weight of the magnet, i.e. to between 90% and 110% of the weight of the magnet, and is arranged eccentrically on the motor shaft on an opposite side from the magnet.

This refinement has the advantage of preventing drive imbalances and thus ensuring higher speeds. The noise caused by the drive may thereby likewise also be minimized. It goes without saying, in any event, that the overall mechanical stability of the drive is also improved thereby.

The apparatus according to the invention furthermore preferably comprises a control unit for controlling the motor, wherein the control unit is designed to operate the motor at a first nominal speed, wherein the first nominal speed is selected to be between 1,500 and 2,500 revolutions per minute.

It should be noted that the term "first nominal speed" is used here merely to distinguish it from a "second nominal speed" explained in greater detail below. This terminology is not intended, however, to imply any order, priority or other meaning.

A nominal speed of 1,800 to 2,800 revolutions per minute has proven to be particularly preferred. It has been found that in this speed range an optimum comminution effect is achieved for the salt crystals located in the receiving vessel.

According to a further refinement, the control unit is designed to change the nominal speed of the motor at regular intervals temporarily to a second nominal speed and then in each case to return to the first nominal speed, wherein the second nominal speed is greater than the first nominal speed.

The magnet driven by the motor is thus temporarily accelerated to a greater extent at regular intervals, preferably to beyond the maximum of the above-mentioned speed ranges. The consequence of this is that the magnetic force acting on the ball is no longer sufficient to force the ball to rotate jointly with the magnet driven by the motor. The ball can therefore no longer follow the rotating magnet exactly and is caused to leave its circular path. This may result in a type of wobbling by the ball within the receiving vessel. The particular advantage of this procedure is that accumulations of salt in the middle of the receiving vessel are carried along by the ball and fed to the comminution process. The subsequent return to the first nominal speed brings the ball back to its circular path within the receiving vessel.

The apparatus preferably has an input device for the user to define the first nominal speed. This allows the user to regulate the intensity with which the generated salt aerosol flows out of the apparatus. The quantity of outflowing salt aerosol may thus for example be adapted to the size of the space in which the apparatus has been set up. The first nominal speed may conceivably be set via one or more selector switches.

Alternatively or in addition to the latter refinement, the apparatus may comprise a temperature sensor for generating a temperature signal and a hygrometer for generating a humidity signal, wherein the control unit is designed to regulate the first nominal speed as a function of the temperature signal and of the humidity signal. The control unit is preferably designed to switch off the motor if a predefined temperature and/or humidity threshold value is exceeded. This serves in particular to prevent damage and malfunctions.

The advantage of this refinement is that the intensity of the salt aerosol flowing out of the apparatus is regulated automatically. This is advantageous in particular because the ambient climate is critical for the properties of the salt aerosol. Too damp an indoor climate prevents the apparatus according to the invention from functioning properly. Too hot an ambient climate may result in damage to various electrical and mechanical parts of the apparatus. To avoid malfunctioning or damage, provision may therefore be made for the control unit to be designed to switch off the apparatus if a temperature and/or humidity threshold value is reached.

According to a further refinement of the present invention, the ascending pipe is preferably curved.

The curvature of the ascending pipe in particular offers the possibility of a space-saving arrangement, without having to reduce the effective length of the ascending pipe. With a 90° curvature of the ascending pipe, the lower part of the ascending pipe connected to the receiving vessel may be vertically oriented, wherein the micronized salt particles exiting the apparatus exit horizontally from the outlet orifice arranged at the upper end of the ascending pipe.

According to a further refinement, the receiving vessel is arranged detachably on the housing.

To fill the receiving vessel with salt, the latter may thus be separated from the housing. This also makes it easier to clean the receiving vessel.

According to a further refinement of the present invention, provision is furthermore made for the apparatus to comprise lighting for illuminating the interior of the receiving vessel and/or for illuminating the outlet orifice.

The advantage of illuminating the interior of the receiving vessel is that the filling level of the salt located in the receiving vessel may be readily seen by the user. By illuminating the outlet orifice, the micronized salt particles exiting from the apparatus may be better observed.

It goes without saying that the above-mentioned features and those still to be explained below may be used not only in the respectively stated combination but also in other combinations or alone, without going beyond the scope of the present invention.

One exemplary embodiment of the invention is explained in greater detail in the following description and illustrated in the drawings, in which:

FIGS. 1-6 show different views of an exemplary embodiment of the apparatus according to the invention. The apparatus is designated overall therein with reference numeral 10.

Figure 1:
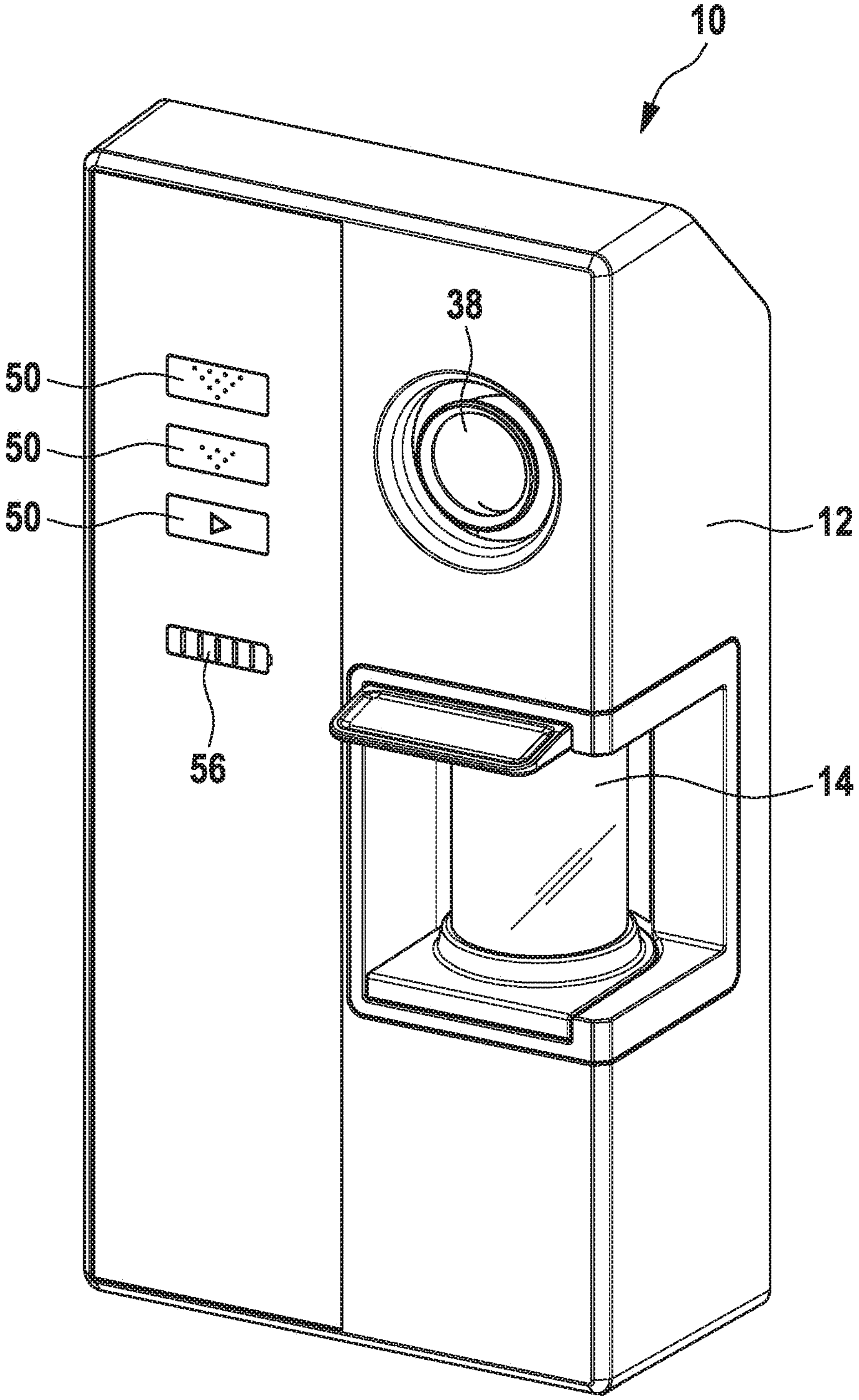
FIG. 1 is a perspective view of an exemplary embodiment of the apparatus according to the invention.
Figure 2:
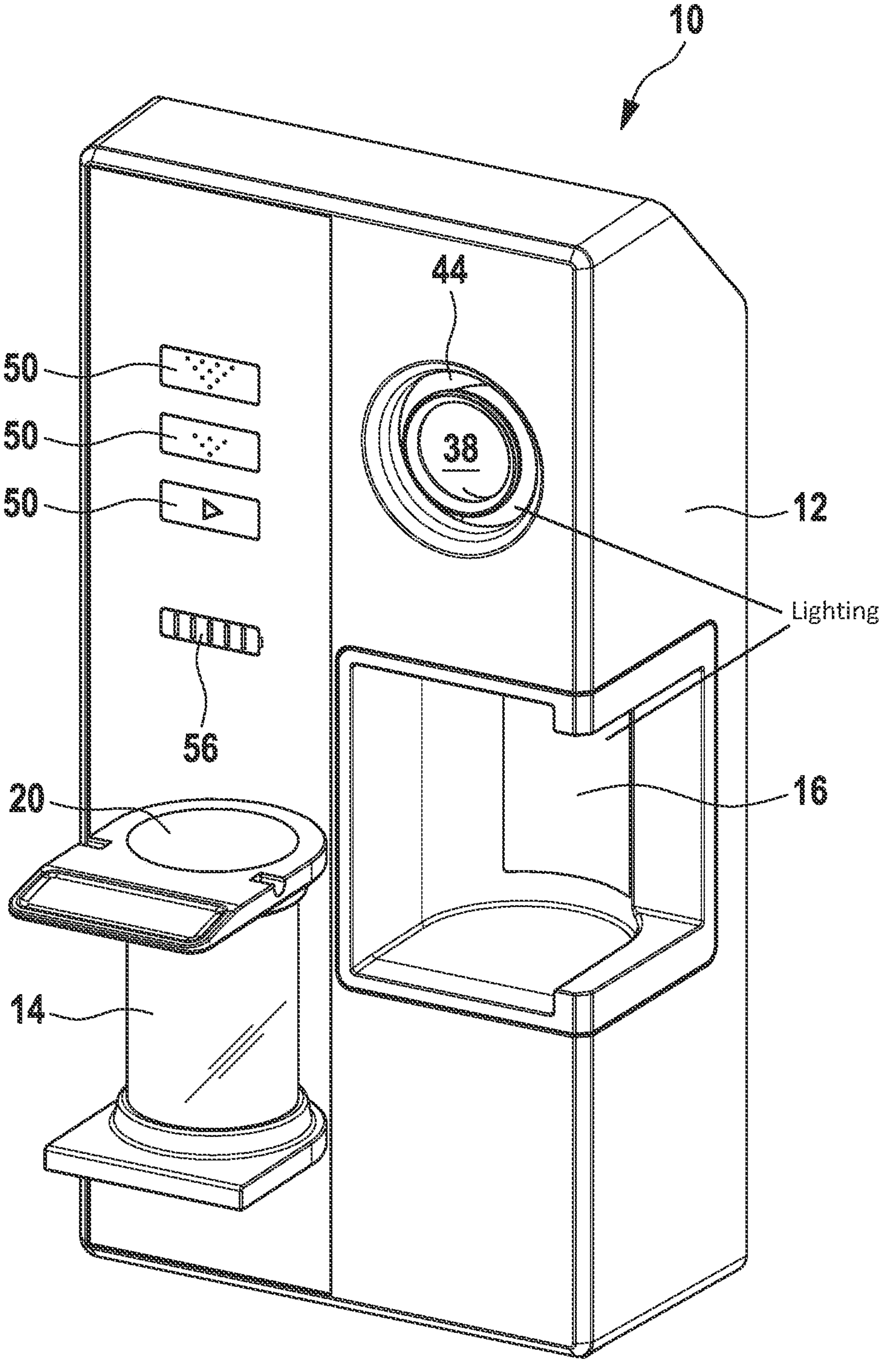
FIG. 2 is a further perspective view of the exemplary embodiment shown in FIG. 1 of the apparatus according to the invention, wherein, in comparison with FIG. 1, a receiving vessel belonging to the apparatus has been detached from the housing of the apparatus.
Figure 3:
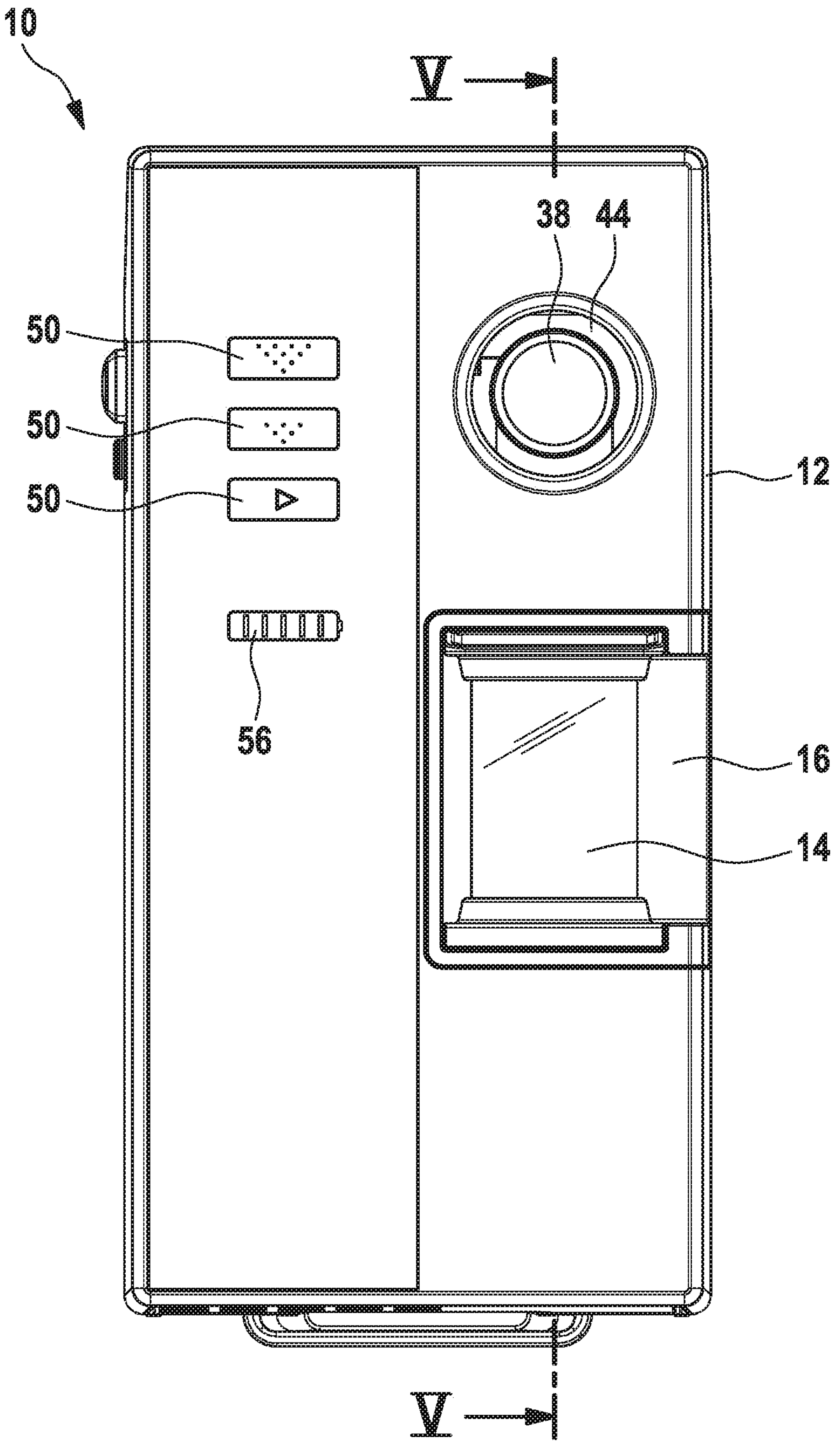
FIG. 3 is a plan view from the front of the exemplary embodiment shown in FIG. 1 of the apparatus according to the invention.

The apparatus 10 comprises a housing 12 and a receiving vessel 14, which may preferably be attached detachably to the housing 12. To this end, a cavity or recess 16 is provided on the front of the housing 12 into which the receiving vessel 14 may be inserted, preferably form-fittingly.

The receiving vessel 14 serves to receive grains of salt 46, which are to be micronized using the apparatus 10 to produce a salt aerosol. The receiving vessel 14 preferably has a cylindrical shape with a closed, circular bottom face 18. The receiving vessel 14 is preferably open at the top. The salt particles 54 comminuted in the receiving vessel 14 may thus exit through an orifice 20 at the top of the receiving vessel 14 during operation of the apparatus 10.

Figure 4:
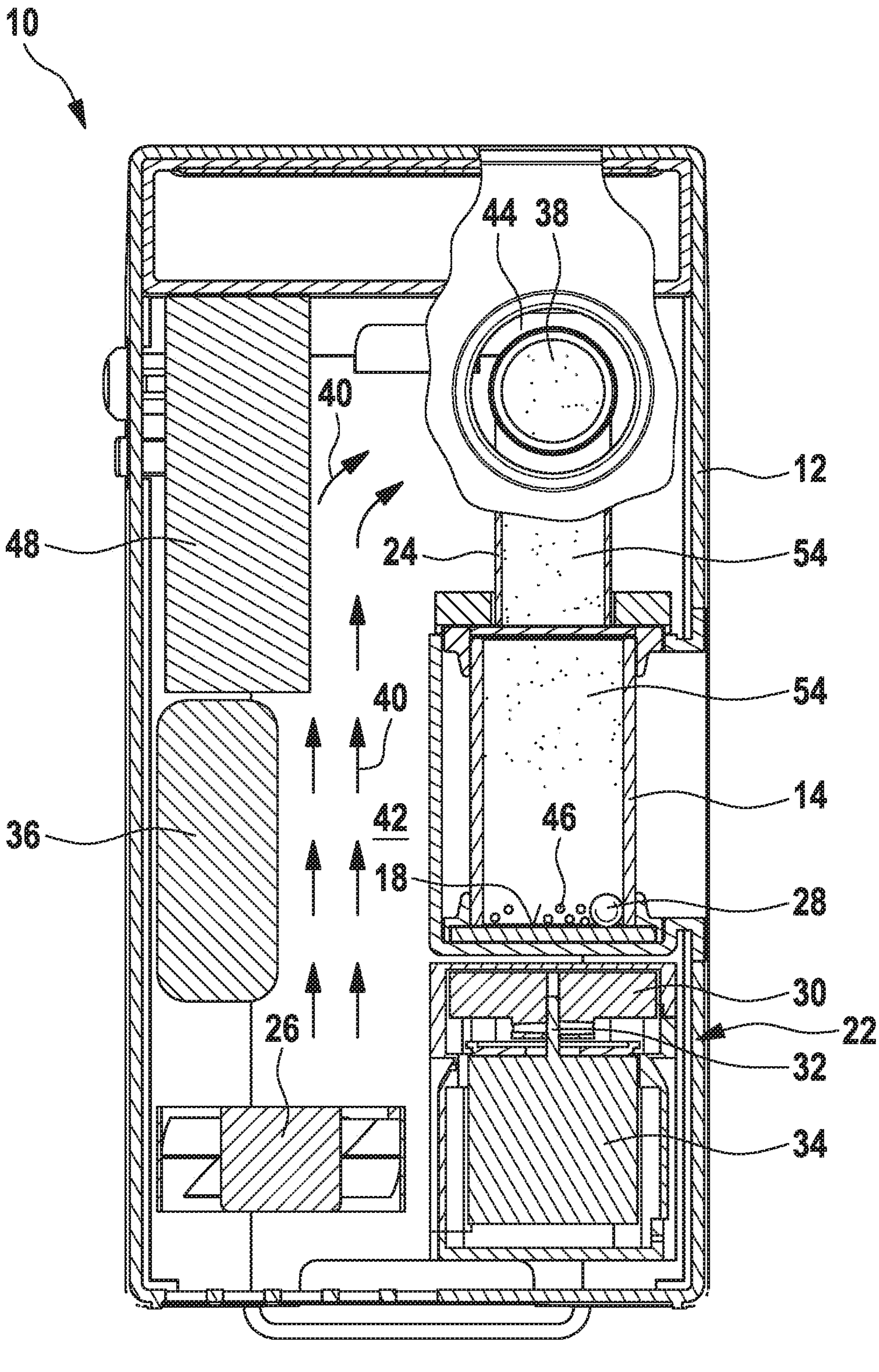
FIG. 4 is a cross-sectional view of the exemplary embodiment shown in FIG. 1 of the apparatus according to the invention.
Figure 5:
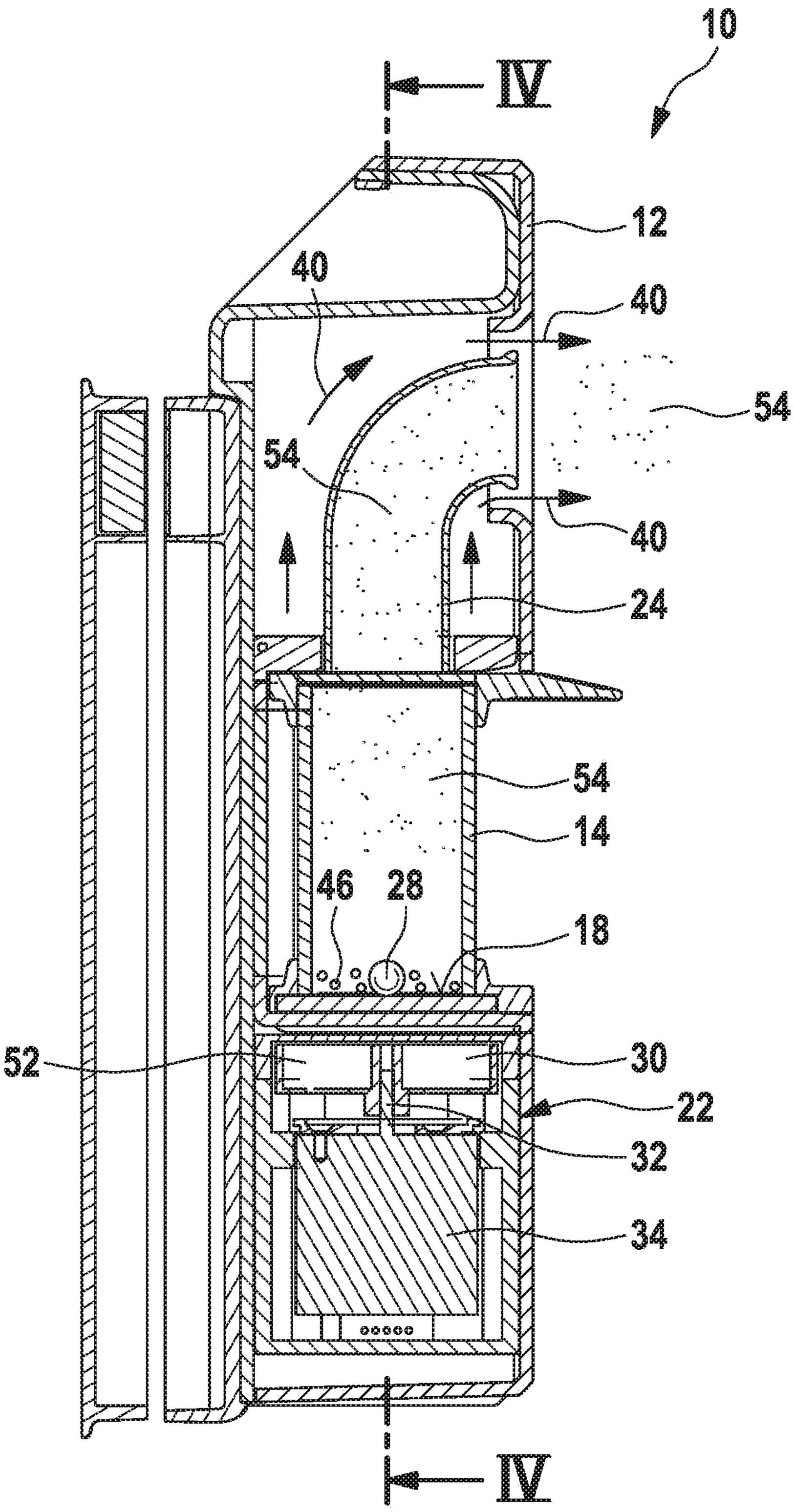
FIG. 5 is a longitudinal sectional view of the exemplary embodiment shown in FIG. 1 of the apparatus according to the invention.
Figure 6:
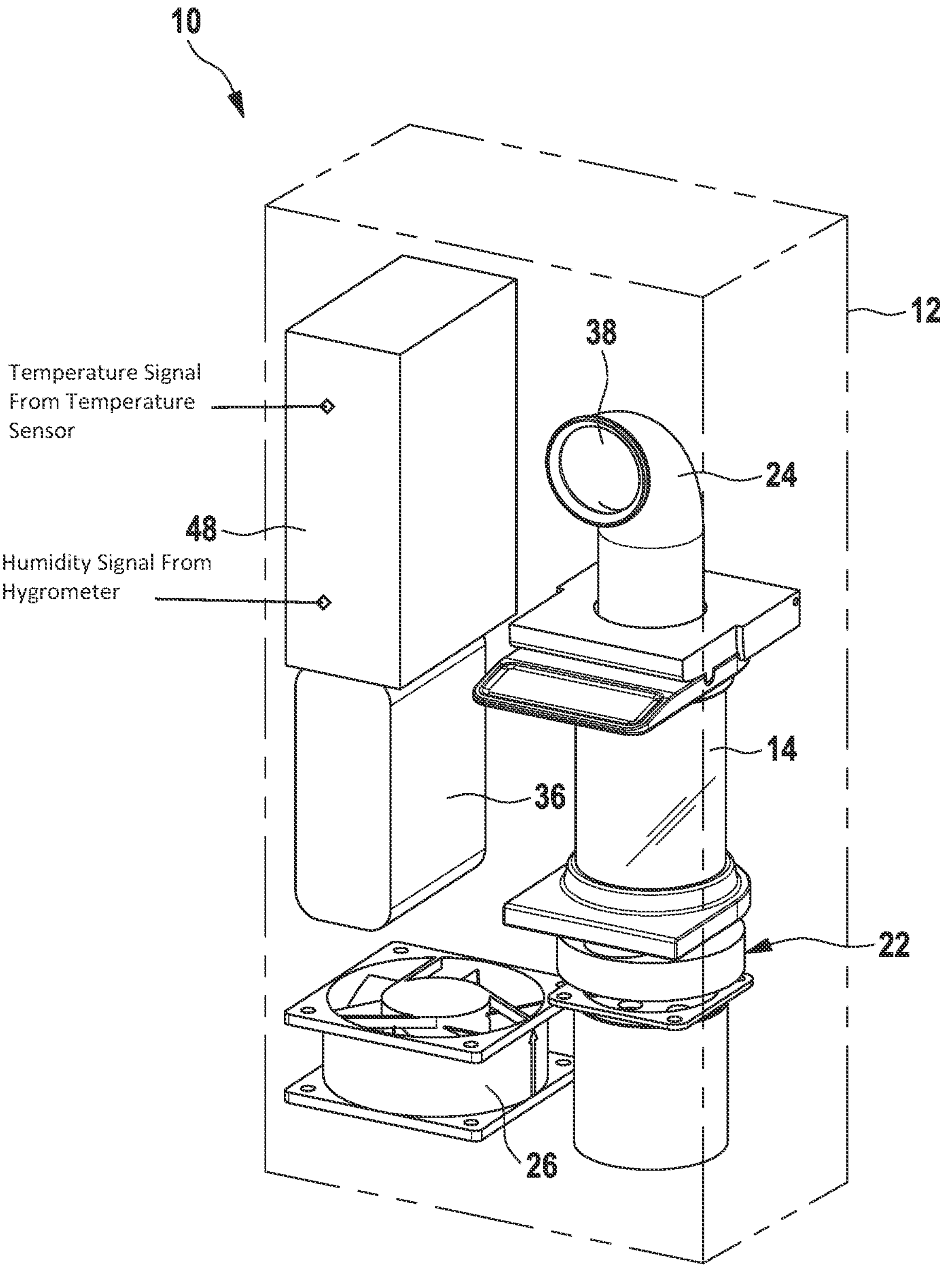
FIG. 6 is a perspective internal view of the exemplary embodiment shown in FIG. 1 of the apparatus according to the invention, wherein the housing is hidden or only shown schematically.

The apparatus according to the invention 10 further comprises a grinding unit 22, an ascending pipe 24 and a fan 26, which are preferably all arranged within the housing 12 (see FIGS. 4-6).

The grinding unit 22 serves in comminuting the salt 46 to be micronized and located in the receiving vessel 14, i.e. to form micronized salt particles 54. In the exemplary embodiment shown here, the grinding unit 22 comprises a magnetically driven ball 28, which has been inserted detachably into the receiving vessel 14. The ball 28 is moved on a circular path within the receiving vessel 14 by means of a rotationally driven magnet 30 during operation of the apparatus 10. To this end, the magnet 30 is attached eccentrically to a motor shaft 32 of an electrical drive motor 34. The electric motor 34 is preferably supplied with power via an energy storage means 36 likewise incorporated in the housing 12, which means for example comprises a storage battery.

The ascending pipe 24 is connected fluidically with the interior of the receiving vessel 14. It serves to transport the salt particles micronized by the grinding unit 22 in the interior of the receiving vessel 14 outwards out of the apparatus 10. When viewed in the direction of flow of the micronized salt particles, the ascending pipe 24 is thus arranged downstream relative to the receiving vessel 14. The lower part of the ascending pipe 24, which is connected to the receiving vessel 14, is preferably arranged coaxially relative to the receiving vessel 14. The upper part of the ascending pipe 24 is preferably curved. Although an uncurved ascending pipe could in principle also be considered, a curved ascending pipe has the advantage, compared with an uncurved ascending pipe, of lower structural height for the same effective length.

At the end remote from the receiving vessel 14, the ascending pipe 24 comprises an outlet orifice 38 through which the micronized salt particles 54 may flow outwards out of the apparatus 10.

The fan 26, which preferably takes the form of a ventilating fan, generates an air stream inside the housing 12 which is indicated schematically with arrows 40 (see FIGS.

4 and 5). The fan 26 is preferably designed to generate a volumetric flow rate in the range from 10-20 m3/h. An essential feature of this air stream 40 is that it does not, as is generally conventional for such micronizers, flow through the receiving vessel 14, but rather is conveyed inside the housing 12 past the receiving vessel 14 by an air duct 42 not described in any greater detail here. The air duct 42 opens at the opposite end from the fan 26 into an air outlet 44. This air outlet 44 is preferably arranged concentrically with the outlet orifice 38 of the ascending pipe 24. The air outlet 44 preferably completely surrounds the outlet orifice 38. Both the outlet orifice 38 and the air outlet 44 preferably have a round outer contour. The concentric arrangement thereof thus results in a roughly circular ring-shaped cross-section for the air outlet 44.

The mode of operation of the apparatus 10 is best understood with reference to FIGS. 4 and 5.

First of all, the salt 46 loaded into the receiving vessel 14 before the start of operation is comminuted or micronized by means of the grinding unit 22. To this end, the magnet 30 is rotated by means of the electric motor 34. The motor 34 is in this case controlled by a control unit 48 which regulates the nominal speed of the motor preferably to 1,500 to 2,500 revolutions per minute. Using selector switches 50, which are mounted on the outside of the housing 12 and in this case generally designated input devices, the speed of the motor 34 may be adjusted stepwise by the user. In this way, the current intensity of the generated salt aerosol may be adjusted by the user. Continuous speed adjustment, for example by a rotary knob, is in principle also conceivable.

The ball 28 located in the receiving vessel 14 is carried along by the rotation of the magnet 30, such that the ball rotates approximately synchronously with the magnet 30 within the receiving vessel 14. To compensate the centrifugal forces arising as a result of movement of the magnet 30, a counterweight 52 is preferably mounted on the motor shaft 32 on the opposite side from the magnet 30. Instead of this counterweight 52, a second magnet may also be arranged at this position.

The comminution process of the salt crystals 46 caused by movement of the ball 28 is based on multiple effects: on the one hand, the salt crystals 46 are set in motion by the rotation of the ball 28 and tossed around inside the receiving vessel 14. Some salt crystals thereby impact against one another. Others in turn thereby impact against the internal wall of the receiving vessel 14. Still other salt crystals are ground between the ball 28 and the internal wall of the receiving vessel 14. It has been found that, due to these effects taking place together, the salt crystal 46 comminution process is very efficient.

The comminuted or micronized salt crystals, which are indicated schematically in FIGS. 4 and 5 and are provided with reference numeral 54, are flung upwards by the movement of the ball 28 inside the receiving vessel 14. Provided these are sufficiently small, they may ascend in the receiving vessel 14 and within the adjoining ascending pipe 24 contrary to the effect of the gravitational force. The air stream 40 generated by the fan 26 generates a type of suction flow in the region of the outlet orifice 38 as a result of the above-described flow around the ascending pipe 24. This suction flow is induced inside the ascending pipe 24 in particular in the region of the outlet orifice 38. It is thus ensured that only the micronized salt particles 54 which have ascended inside the receiving vessel 14 and inside the ascending pipe 24 against the effect of the gravitational force are caught up by the suction flow and flow out of the outlet orifice 38 and thus of the apparatus 10. Larger salt particles, on the other hand, which remain on the bottom of the receiving vessel 14 due to their weight or at least do not ascend as far as into the upper region of the ascending pipe 24, are not caught up by the suction generated in the ascending pipe 24 by the air stream 40 and thus remain in the apparatus 10.

To prevent larger salt crystals which are not caught up by the rotating ball from settling permanently in the middle of the bottom of the receiving vessel 14, provision is preferably made for the control unit 48 to increase the nominal speed of the motor 34 at regular intervals temporarily to above a defined threshold value. If namely a given speed of the motor 34 is exceeded, the force acting between the ball 28 and the magnet 30 is namely no longer sufficient for the ball 28 to be able to follow the rotation of the magnet 30. The ball 28 then begins to "prance about" on the bottom face 18 of the receiving vessel 14. In the process, it moves over regions of the bottom face 18, in particular also the middle of the bottom face 18, which it does not otherwise reach during its conventional rotation along the outer edge of the bottom face 18. The salt crystals located at these points are then thus likewise caught up. The above-stated temporary increase in speed preferably takes place for just a few seconds.

The following features may also be provided: an indicator 56 may be provided on the outside of the housing 12 for indicating the storage battery 36 level. In addition, the apparatus 10 may optionally comprise lighting, not shown in the drawings for the sake of simplicity, which serves to illuminate the outlet orifice 38 and/or the interior of the receiving vessel 14. Moreover, the apparatus 10 optionally comprises a temperature sensor and a hygrometer, wherein the control unit 48 is in this case designed to regulate the speed of the motor 34 as a function of the temperature signal generated by the temperature sensor and/or the humidity signal generated by the hygrometer. The control unit 48 is preferably designed to switch off the motor 34 if a predefined temperature and/or humidity threshold value is exceeded. This serves in particular to prevent damage and malfunctions.

The invention claimed is:

1. An apparatus configured to micronize an inorganic salt, comprising:

a receiving vessel configured to receive the inorganic salt to be micronized in an interior of the receiving vessel;

a grinding unit configured to comminute the inorganic salt to be micronized located in the receiving vessel and to form micronized salt particles, wherein the grinding unit comprises a motor, a magnet driven rationally by the motor, and a ball of magnetizable material, wherein the ball is arranged in the receiving vessel, and wherein the motor and the magnet are arranged outside the receiving vessel;

an ascending pipe having a lower end and an upper end, wherein the ascending pipe is at its lower end connected fluidically to the receiving vessel and serves to transport the micronized salt particles, wherein at the upper end of the ascending pipe, an outlet orifice is arranged through which the micronized salt particles can flow out of the apparatus;

a fan configured to generate an air stream;

a housing with an air outlet through which the air stream leaves the apparatus, and with an air duct connecting the fan to the air outlet, wherein a lower end of the air duct is connected to the fan, and wherein the air owlet is arranged at an upper end of the air duct, wherein the air duct is separated by at least one wall from the interior of the receiving vessel, such that the air stream generated by the fan does not flow through the interior of the receiving vessel, and wherein the air outlet at least partly surrounds the upper end of the ascending pipe at the upper end of the air duct;

a temperature sensor configured to generate a temperature signal;

a hygrometer configured to generate a humidity signal; and a control unit with a switch that control the motor, wherein the control unit is configured to operate the motor at the first nominal speed, wherein the first nominal speed is selected to be between 1,500 and 2,500 revolutions per minute, wherein the control unit and the switch are configured to control the first nominal speed as a function of the temperature signal and of the humidity signal.

2. The apparatus as claimed in claim 1, wherein the air outlet is arranged concentrically with the outlet orifice and completely surrounds the outlet orifice.

3. The apparatus as claimed in claim 1, wherein the grinding unit comprises precisely one ball of magnetizable material.

4. The apparatus as claimed in claim 1, wherein the receiving vessel has a closed, round bottom face.

5. The apparatus as claimed in claim 4, wherein a diameter of the bottom face corresponds to at least 5 times a diameter of the ball.

6. The apparatus as claimed in claim 1, wherein the motor has a motor shaft on which the magnet is eccentrically arranged.

7. The apparatus as claimed in claim 6, wherein the grinding unit has a counterweight which corresponds to between 90% and 110% of a weight of the magnet, and is arranged eccentrically on the motor shaft on an opposite side from the magnet.

8. The apparatus as claimed in claim 1, wherein the control unit is configured to control the motor to change at regular intervals temporarily from the first nominal speed to a second nominal speed and then in each case to return to the first nominal speed, wherein the second nominal speed is greater than the first nominal speed.

9. The apparatus as claimed in claim 1, wherein the apparatus has an input device for a user to define the first nominal speed.

10. The apparatus as claimed in claim 1, wherein the ascending pipe is curved.

11. The apparatus as claimed in claim 1, wherein the receiving vessel is arranged detachably on the housing.

12. The apparatus as claimed in claim 1, wherein the apparatus comprises lighting configured to illuminate the interior of the receiving vessel and/or to illuminate the outlet orifice.

13. An apparatus configured to micronize an inorganic salt, comprising:

a receiving vessel configured to receive the inorganic salt to be micronized in an interior of the receiving vessel;

a grinding unit configured to comminute the inorganic salt to be micronized located in the receiving vessel and to form micronized salt particles;

an ascending pipe having a lower end and an upper end, wherein the ascending pipe is at its lower end connected fluidically to the receiving vessel and serves to transport the micronized salt particles, wherein at the upper end of the ascending pipe, an outlet orifice is arranged through which the micronized salt particles can flow out of the apparatus;

a fan configured to generate an air stream; and a housing with an air outlet through which the air stream leaves the apparatus, and with an air duct connecting the fan to the air outlet, wherein a lower end of the air duct is connected to the fan, and wherein the air outlet is arranged at an upper end of the air duct, wherein the air duct is separated by at least one wall from the interior of the receiving vessel, such that the air stream generated by the fan does not flow through the interior of the receiving vessel, wherein each of the air outlet and the outlet orifice is circular, and wherein the air outlet has a larger diameter than the outlet orifice, is arranged concentrically with the outlet orifice and completely surrounds the outlet orifice.

* * * * *